US005684112A

United States Patent [19]

Berthiaume et al.

[11] Patent Number: 5,684,112

[45] Date of Patent: Nov. 4, 1997

[54] LOW VISCOSITY ORGANOFUNCTIONALIZED SILOXYSILICATES AND COSMETIC FORMULATIONS THEREWITH

[75] Inventors: Marianne D. Berthiaume, Latham; Peter M. Miranda, Glenville, both of N.Y.

[73] Assignee: General Electric Company, Pittsfield, Mass.

[21] Appl. No.: 640,400

[22] Filed: Apr. 30, 1996

Related U.S. Application Data

[63] Continuation of Ser. No. 386,899, Feb. 10, 1995, abandoned.

[51] Int. Cl.$^6$ .................. C08G 77/08

[52] U.S. Cl. .................. 528/29; 528/31; 528/39; 556/445; 424/70.12

[58] Field of Search .................. 528/39, 31, 29; 556/445; 424/70.12

[56] References Cited

U.S. PATENT DOCUMENTS

| | | | |
|---|---|---|---|
| 3,541,127 | 11/1970 | Hughes et al. | 528/39 |
| 3,772,247 | 11/1973 | Flannigan | 260/46.5 H |
| 3,887,601 | 6/1975 | Kanner et al. | 528/39 |
| 3,975,361 | 8/1976 | Poy | 528/39 |
| 4,774,310 | 9/1988 | Butler | 528/23 |
| 5,011,901 | 4/1991 | Fukutani | 528/42 |
| 5,235,004 | 8/1993 | Kobayashi et al. | 525/477 |
| 5,246,996 | 9/1993 | McVie et al. | 524/265 |
| 5,334,737 | 8/1994 | Thimineur et al. | 556/440 |
| 5,373,078 | 12/1994 | Juen et al. | 528/15 |

FOREIGN PATENT DOCUMENTS

| | | |
|---|---|---|
| 0251435 | 1/1988 | European Pat. Off. . |
| 342648 | 11/1989 | European Pat. Off. . |
| 0555050 | 8/1993 | European Pat. Off. . |
| 0632099 | 1/1995 | European Pat. Off. . |

*Primary Examiner*—Margaret W. Glass
*Attorney, Agent, or Firm*—Kenneth S. Wheelock

[57] ABSTRACT

Low viscosity MQ silicone resins as a composition of matter, methods of preparation of same and cosmetic and personal care products comprising said MQ resins.

7 Claims, No Drawings

LOW VISCOSITY ORGANOFUNCTIONALIZED SILOXYSILICATES AND COSMETIC FORMULATIONS THEREWITH

This is a continuation of application Ser. No. 08/386,899 filed on Feb. 10, 1995, now abandoned.

FIELD OF THE INVENTION

The present invention relates to MQ silicone resins that are a new composition of matter, siloxysilicates wherein said siloxysilicates resins have desirable physical properties that render them particularly suitable for certain personal care products such as skin care products, color cosmetic products, hair conditioners, hair cremes (alternatively spelled creams), hair bodying agents, curl retention, and luster enhancers.

BACKGROUND OF THE INVENTION

This invention relates to new organosilicone resins and cosmetic products derived therefrom, in particular hair care products comprising the new organosilicone resins, MQ siloxysilicates, and to new cosmetic formulations specific thereto.

Siloxane resins consisting of triorganosiloxane units and silicon dioxide units are known, commercially available materials and are employed in the formulation of silicone products such as adhesives and anti foams. Such resins are sometimes referred to as MQ resins in view of the presence of the monovalent (M) siloxane units and the quadrivalent or tetravalent (Q) silicon dioxide units.

In view of the reactivity of the silyl hydride group, it is sometimes desired to include such groups in resins of the MQ type. Siloxane resins composed of silicon dioxide units and units of the general formula $HR_2SiO_{1/2}$ where R represents hydrogen, a monovalent hydrocarbon or monovalent halohydrocarbon group are frequently utilized because of the high reactivity of the silyl hydride functionality therein. Such resins have been used for organopolysiloxane elastomers. As precursors to other synthetic silicones, it is frequently desirable that these resins contain a limited number of silyl hydride groups. U.S. Pat. No. 3,772,247 discloses organopolysiloxane resins consisting of $R'_3SiO_{1/2}$ units, $SiO_2$ units and units of the type HR'SiO and/or $HSiO_{1.5}$ in which R' represents a monovalent hydrocarbon group selected from the group consisting of alkyl, aryl, alkaryl, alkenyl, cycloalkyl, or cycloalkenyl groups. While such resins possess silyl hydride groups they posses a significant and measurable level of divalent or trivalent organosiloxyl groups.

U.S. Pat. No. 4,774,310 ('310) discloses MQ resins consisting of $R_3SiO_{1/2}$ units and $SiO_2$ units where R is essentially defined as above. The MQ resins of the '310 patent are further reacted with disiloxanes under conditions of acidic catalysis to produce MQ type siloxane resins where the ratio M/Q is in the range of 0.4:1 to 1:1 and where the fraction of hydride stopped units of the general formula $H_aR_{3-a}SiO_{1/2}$ ranges from 0.1 to 30 percent of the total number of M (monovalent) units present.

Silicones have properties that make them particularly advantageous in hair cosmetic products. Certain silicones produce uniform thin films that are hydrophobic and also produce solutions or emulsions that posses a low viscosity. The low viscosity property allows higher loadings of active ingredients in a cosmetic product without the deleterious effects normally associated with high viscosity products, difficulty of pumping or erratic spray patterns. This is important to the consumer because preparations that are hard to use or erratic in delivery from the dispensing apparatus will not be preferred.

The cosmetic and toiletry industry has produced a wide range of grooming aids that utilize silicones. Among the various products are shampoos to clean the hair and scalp, hair rinses, conditioners, dressings, sprays, wave sets, coloring and bleaching preparations, permanent waves, and hair straighting and strengthening compositions. Cleanliness of hair and scalp are important personal grooming criteria. Soiled hair takes on a lackluster appearance and becomes oily and unpleasant to the touch. Consumers desire a shampoo that foams quickly and copiously and rinses thoroughly leaving the hair with a fresh clean smell and in a manageable state. Further, consumers tend to prefer those shampoos that also leave the hair soft, shiny, lustrous, and full bodied. Shampoos are available in a variety of formulations as clear or opaque liquids, gels, or pastes. In order to fulfill the various criteria demanded by the consuming public, shampoo formulations contain one or more cleansing agents such as nonionic, anionic, amphoteric, and cationic surfactants along with various optional additives that include among others viscosity control agents, conditioners, preservatives, fragrances, vitamins, antioxidants opacifiers, pearling agents, sunscreens, and botanicals as well as functionalizing additives such as conditioners, shine enhancers, and body agents. After shampooing, the hair is usually wet, frequently tangled and thus difficult to comb. Thus it is common for consumers to apply rinses and conditioners to enhance the ease of combing and detangling, to increase hair body, to improve shine and texture, to prevent static buildup, to impart manageability, style retention, and curl retention.

Hair body is a subjective and poorly defined quality. It is generally accepted that volume is related to or provides a means for quantitatively measuring hair body. One method to increase the volume of hair tresses (and consequently the subjective property of hair body) is to impart a small degree of triboelectric charging to the hair. This can be accomplished through the use of a so-called volumizing shampoo which generally functions to strip the hair of natural oils leaving the hair fibers negatively charged with a consequent tendency for the hair fibers to electrostatically repel one another. This method does not produce consistent or predictable results since small changes in humidity will either aggravate the triboelectric charging resulting in fly-away hair (low RID or dissipate the electrostatic charge resulting in flat hair (high RH). This technique also has a tendency to raise the cuticle scales damaging the hair and rendering it difficult to comb making it unmanageable. A more preferable technique to impart hair body is to deposit a hydrocarbon-based film on the hair via a preparation that remains on the hair between shampoos. These preparations, typically incorporating a hydrocarbon resin, generally impart drag and increase the forces necessary to comb the hair and thus make the hair difficult to groom while maintaining style. Additionally such products, depending on the choice of resins and base solvents can also result in the appearance of unsightly flakes on the hair. An additional problem is that such hydrocarbon solvent resin mixtures can dry the hair or impart brittleness, resulting in hair fiber breakage during subsequent grooming.

When using hydrocarbon based conditioning agents, increasing the organoalkyl content of quaternary ammonium conditioning compounds imparts an increasing conditioning ability to the compound. Conditioning efficacy of a quaternary ammonium compound increases with increasing alkyl chain length or with increasing alkyl substitution according to the series mono-alkyl<di-alkyl<tri-alkyl Generally products that condition hair do not impart an improved body or hair volume unless they also contain resins.

One use of polymeric dialkylsiloxanes is to impart a conditioning property to hair care products. While the conventional polymeric dialkylsiloxanes impart good conditioning properties, such materials have a tendency to interact antagonistically with other additives such as fixatives diminishing their effectiveness. This conflict in properties between ingredients results in reformulations and stimulates efforts to prepare new materials that will be more compatible.

Conditioning shampoos are generally formulated to provide a cleansing of the hair followed by deposition of a material that acts to provide a conditioning benefit. Incorporation of a volumizing organofunctional MQ silicone resin that is compatible with the other components of a 2-in-1 shampoo, provides cleansing, conditioning and volumizing benefits, unlike prior art formulations.

Fixatives are generally designed to provide a temporary setting effect or maintain curl to the hair, the most common being a hair spray intended for use after the hair has been dried. Other fixatives may be used after the hair is towel dried to provide more body and volume and to aid in styling. Specialty type fixatives such as the foregoing include styling gels, mousses, cremes, foams, spritzes, mists, glazes, glossing gels, shaping gels, sculpting mousses, and setting gels among others. These fixatives should be compatible with a subsequent use of a fixative or luster enhancing hair spray.

Cuticle coats are formulations designed to impart or enhance shine on hair. Additionally, cuticle coats frequently reduce both tribo-electric charging effects, i.e. fly-away hair, and combing forces, by adding a lubricious coating to the hair, thus lowering beth interfiber friction and electrostatic repulsion between the fibers. One method of imparting or increasing apparent luster or gloss on the hair is to coat the hair with a material having a high refractive index. Using this technique, the apparent gloss or shine will be proportional to the refractive index of the material on the fiber surface. Absent other factors, a direct proportionality exists between refractive index and apparent shine on hair. Thus higher refractive index cuticle coating formulations will tend to impart a higher shine on hair.

SUMMARY OF THE INVENTION

The present invention concerns MQ resins of the formula:

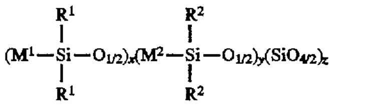

where beth $R^1$ and $R^2$ may be either a phenyl group or an alkyl group having from 1 to 12 carbon atoms, and beth $M^1$ and $M^2$ may independently be phenyl, phenethyl, polyether, hydrogen, or one to twenty-three carbon atom alkyl group (which may variously include halogen substituted hydrocarbon radicals) in any combination subject to the limitation that the ratio of the subscripts x, y, and z satisfies the following relationship:

$$0.5 \leq (x+y)/z \leq 4.0.$$

The MQ resin itself is a polymer composed of a distribution of exemplary species having a range of molecular weights. The MQ resin can be defined in a specific instance by setting the value for z equal to unity. Thus, when z=1, x ranges from between 0 and 4, and y ranges from between 0 and 4. It is also preferred that the ratio of (x+y)/z be equal to about 2. In the complex mixture of compounds, typically referred to as a resin, defined by the above general formula, z ranges from 1 to about 30 and x and y may be zero or a positive number.

The polyether MQ resin of the present invention is also useful as an emulsifying agent for oil-in-water emulsions. Such oil-in-water emulsions are particularly useful in a wide variety of cosmetic products.

The resins of the present invention are useful in personal care formulations and cosmetics. More particularly the resins are useful in hair care formulations to impart improved shine on hair, increased volume or body, reduced combing force and curl retention.

DETAILED DESCRIPTION OF THE INVENTION

The present invention relates to functionalized MQ silicone resins having the general formula:

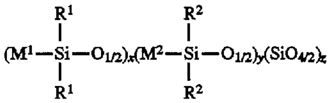

1)

where both $R^1$ and $R^2$ may be either a phenyl group or an alkyl group having from 1 to 12 carbon atoms, and both $M^1$ and $M^2$ may independently be phenyl, phenethyl, polyether, hydrogen, or one to twenty-three carbon atom alkyl group (which may variously include halogen substituted hydrocarbon radicals) in any combination subject to the limitation that the ratio of the subscripts x, y, and z satisfies the following relationship:

$$0.5 \leq (x+y)/z \leq 4.0. \qquad 2)$$

The MQ resin itself is a polymer composed of a distribution of exemplary species having a range of molecular weights. The MQ resin can be defined as a molecular species in a specific instance by setting the value for z equal to unity. Thus, when z=1, x ranges from between 0 and 4, and y ranges from between 0 and 4. It is also preferred that the ratio of (x+y)/z be equal to about 2, this is true for mixtures of the MQ species comprising the resin. A preferred resin is satisfied by the following values for the subscripts x, y, and z; x=2, y=0, and z=1 when $R^1=CH_3$.

When $M^1$ and/or $M^2$ is a polyether, the polyether has the general formula:

$$H_2C{=}C{-}CH_2R^3{-}(O{-}CHR^4{-}CH_2)_u{-}(OCH_2CH_2)_v{-}OR^5$$

where $R^3$ is $-(CH_2)_n-$ with n ranging from 1 to about 20, $R^4$ is a one to twenty carbon alkyl group, and $R^5$ is selected from the group consisting of H, $-CH_3$, and $-C(O)CH_3$; and where u and v are integers ranging from 0 to 20 subject to the limitation that $u+v \geq 1$.

The silicone resins of formula 1) are generally prepared via a platinum catalyzed hydrosilylation reaction which typically proceeds as follows:

(reactants)

3)

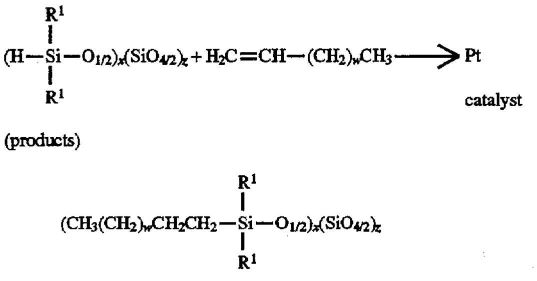

which contains both branched and linear radicals where w typically ranges from 0 to about 20 and the ratio of x/z ranges from 0.5 to about 4.0. While the above described reaction is specific for straight chain alkyl substituted MQ resins, this reaction may be generally employed with substitued terminal olefins of varying structures. The liquids produced by reaction 3) are low viscosity liquids having a viscosity generally ranging from about 50 to 1000 centistokes at 25° C. The low viscosity of these compounds and resins is in contrast to the viscosity of similarly alkyl substituted linear silicones which may be viscous liquids or waxes at 25° C. The platinum catalyzed hydrosilylation between silyl hydrides (alternatively hydride fluids) and a terminal olefin moiety utilized in reaction 3) is well-known and the subject of several U.S. Pat. Nos. 3,159,662; 3,220,972; 3,715,334; 3,775,452; and 3,814,730; herewith incorporated by reference.

The silicon containing starting materials of reaction 3) are generally prepared by the reaction of an alkyl silicate and a dialkylhalosilane. The hydride stopped siloxysilicate starting material is hydrosilylated under the appropriate conditions with a suitable olefin or mixture thereof to prepare the compounds of formula 1). Hydrosilylation with styrene derivatives will produce phenethyl variants of these compounds. Generally, a styrenic compound having the formula:

$$C_6H_5—CR^6═CH_2$$

where $R^6$ is a monovalent radical selected from the group consisting of hydrogen, methyl, and phenyl is used as the starting material for such a hydrosilylation reaction.

The phenethyl substituted siloxysilicates are unique in that they possess higher refractive indices than the alkyl substituted siloxysilicates and they are also miscible in phenyl or phenethyl methyl silicone fluids. This is in sharp contrast to other MQ resins possessing only alkyl substitution which are usually not miscible with phenyl or phenethyl methyl silicone fluids. These phenethyl MQ resins are prepared by a variation of reaction 3):

4)

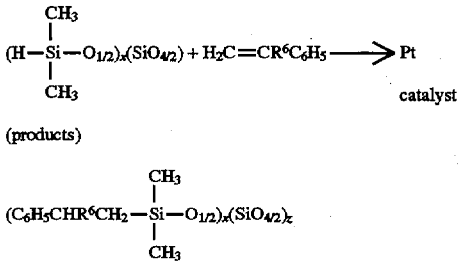

where $R^6$ is selected from the group consisting of hydrogen, methyl, and two to eight carbon alkyl groups.

The siloxysilicate MQ resins of the present invention are useful in a variety of cosmetic and personal care applications, particularly since they are low viscosity fluids having a viscosity ranging from about 50 to 1,000 centistokes at 25° C. This viscosity range, all other chemical factors being constant, tends to vary with the molecular weight of the radicals being substituted into the various pendant groups constituting the MQ resin. Thus, for example higher alkyl or polyether chain lengths, while they might be outside of the specific ranges disclosed and claimed, could conceivably possess viscosities within the disclosed range. Likewise compounds within the disclosed range of alkyl or polyether chain lengths could have viscosities exceeding the disclosed upper limit of 1,000 centistokes. Thus it is applicants intention that the upper limit of 1,000 centistokes as disclosed is an approximate upper limit. While the reductions to practice have emphasized hair care formulations, it is anticipated that the resins of the present invention are useful in a variety of cosmetic formulations including but not limited to skin care, color cosmetics, personal cleansing, and the like. Therefore, in the appended claims, personal care product as a phrase includes these various uses.

EXPERIMENTAL

Preparation of Hydridomethylsiloxysilicate: To 322.1 g of water in a one liter flask was added a mixture containing 123.6 g dimethylchloro-silylhydride, 135.0 g ethylsilicate, and 79.0 g of toluene via an addition funnel. The silane solution was added to the aqueous phase with stirring over a period of 45 minutes. The temperature of the reaction mixture was maintained at or below 60° C. Upon completion of the addition of the silane solution, the mixture was stirred for an additional 10 minutes and then the aqueous phase was removed. The toluene solution was washed with 300 g of water. The organic layer was then stripped by heating to 150° C. and holding at that temperature for two hours at ambient pressure. At the conclusion of the atmospheric pressure strip, the temperature was increased to 165° C. and the toluene was stripped under a vacuum of 200 mm Hg. Theoretical reaction yield was 126.6 g. The product was characterized by infrared spectroscopy noting the absorptions at 2160 $cm^{-1}$ (Si—H) and 1050 $cm^{-1}$ (Si—O—Si).

General Preparation of Alkyldimethylsiloxysilicate; specific example: octadecylhexadecyldimethylsiloxysilicate: 150.0 g of hydrido-dimethylsfloxysilicate containing 1.46 molar equivalents of hydride functionality, 0.98 weight percent is added to a one liter flask followed by the addition of Karstedt's catalysts (as taught in U.S. Pat. No. 3,775,452) in an amount sufficient such that platinum was present at a level of 8 ppm. The mixture was stirred and heated to 45° C. A mixture of 185.1 g of 1-octadecene (0.73 moles) and 164.6 g of 1-hexadecene (0.73) moles was placed in an addition funnel and slowly added to the reaction flask such that the reaction temperature did not exceed 100° C. This procedure required approximately 60 minutes. The reaction was maintained at 120° C. for two hours at which pointed the amount of residual silylhydride had decreased to below 150 ppm, indicating a hydride consumption greater than 95%. The hydride content of the reaction mixture was monitored by infrared spectroscopy. The reaction mixture was then stripped under a vacuum of 5 mm Hg at a temperature of 150° C. until olefins could no longer be detected by gas chromatographic analysis. The resulting product was a clear liquid having a viscosity of 170 centistokes at 25° C. This is Resin A.

Preparation of 1-(2-Phenyl)propyldimethylsfloxysilicate (phenethyl resin): 306.1 g of hydridodimethylsiloxysilicate containing 2.73 molar equivalents of hydride functionality, 0.9 weight percent is added to a one liter flask followed by the addition of Karstedt's catalysts (as taught in U.S. Pat. No. 3,775,452) in an amount sufficient such that platinum was present at a level of 8 ppm. The mixture was stirred and heated to 45° C. 332.7 g (2.82 moles) of α-methylstyrene was placed in an addition funnel and added dropwise so that the reaction temperature never exceed 110° C. This procedure required approximately 90 minutes. The reaction temperature was maintained at 110° C. for between 4 and 6 hours at which the amount of residual silylhydride had decrease to below 250 ppm, indicating reaction of over 95% of the starting hydride. The hydride content of the reaction mixture was monitored by infrared spectroscopy. The reaction mixture was then stripped under a vacuum of 10 mm Hg at a temperature of 150° C. until styrene could no longer be detected by gas chromatographic analysis. The resulting product was a clear liquid having a viscosity of 350 centistokes at 25° C. This is Resin B.

TABLE 1

Refractive Index of Cosmetically Useful Silicone Fluids

| Fluid | Refractive Index $n_D$ at 25° C. |
|---|---|
| Dimethicone (100 cstk) | 1.403 |
| Phenyltrimethicone | 1.459 |
| Resin B | 1.505 |

Preparation of Polyetherdimethylsfloxysilicate: To a 1 liter flask was added 384.3 of an olefin capped polyether, Polyglycol AE501® available from Dow Chemical Co., (0.675 molar equivalent in 10% excess) and 179 g toluene. The solution was warmed to between 45 and 50° C. and Karstedt's catalyst (U.S. Pat. No. 3,775,452) was added to the reaction flask such that the quantity of platinum present was 8 ppm. 64.4 g (0.613 molar equivalent) hydridodimethylsiloxysilicate containing 0.96 wt. % hydride was added to an addition funnel and was added dropwise to the polyether containing solution over a period of about 90 minutes maintaining the reaction temperature at about 70° C. The temperature of the reaction mixture was then increased to 110° C. and stirred for three hours. Afar three hours the quantity of residual silyl hydride was monitored by infrared spectroscopy until the absorbance at 2160 $cm^{-1}$ indicated less than 50 ppm unreacted silyl hydride, i.e. greater than 95% extent of reaction. The reaction mixture was then stripped under a vacuum of 50 mm Hg at 90° C. until the quantity of residual toluene remaining was at or below 50 ppm. The resulting product was a clear liquid with a viscosity of 790 centistokes at 25° C. This is Resin C.

Preparation of Alkyl/Aryl-dimethylsiloxysilicate: 300.0 g of hydrido-dimethylsiloxysilicate containing 2.92 molar equivalents of hydride functionality, 0.98 wt. % was added to a one liter flask followed by the addition of Karstedt's catalyst, as taught in U.S. Pat. No. 3,775,452, in an amount whereby the platinum was present at a level of 8 ppm. The mixture was stirred and heated to 45° C., whereupon 177.3 (1.5 moles) of α-methylstyrene was placed in an addition funnel and added dropwise over a 45 minute period in a fashion whereby the reaction temperature never exceeded 95° C. After maintaining the reaction mixture at 95° C. for a period of 15 minutes, 168.3 g (1.5 moles) of 1-octene was placed in an addition funnel and the 1-octene was added dropwise over a 30 minute period in a fashion whereby the reaction temperature never exceeded 115° C. The reaction mixture was maintained in a temperature range of 100°–110° C. for a period of eight hours, during which period of time the residual hydride content decreased to below 250 ppm, indicative of an extent of reaction in excess of 95%, based on the quantity of starting hydride material. The hydride content of the reaction mixture was monitored by means of infrared spectroscopy. Excess olefinic starting materials were removed by stripping under a vacuum of 10 mm Hg at a temperature of 160° C. until neither styrene nor octene could be detected by gas chromatographic analysis. The resulting transparent liquid had a viscosity of 140 centistokes at 25° C.

Cosmetic Formulation A, Conditioning and Volumizing Effects: An alkyl modified siloxysilicate of the present invention was prepared by reacting a compound of the formula:

$$(H(CH_3)_2SiO_{1/2})_x((CH_3)_3SiO_{1/2})_y(SiO_{4/2})_z$$

where x=2, y=0, and z=1 under hydrosilylation conditions in the presence of a platinum catalyst and a terminal olefin having the formula:

$$H_2C{=}CH(CH_2)_wCH_3$$

which contains both branched and linear radicals where w=15 to produce an MQ siloxysilicate resin of the present invention. This resin, Resin A in the following cosmetic preparation is suitable for use as a hair conditioner:

TABLE 2

Composition of Cosmetic Formulation A1, Conditioner Formulation:

| Component | Amount (Wt. %) |
|---|---|
| Deionized water | 77.77 |
| Cyclomethicone | 4.2 |
| Cetyl Alcohol | 3.2 |
| Resin A (substitutable in succeeding formulations with water, or Resin D) | 3.0 |
| Glycerin | 2.75 |
| Behentrimonium Methosulfate (and) Cetearyl Alcohol | 2.7 |
| Stearamidopropyl Dimethylamine | 2.5 |
| Polysorbate-80 | 1.5 |
| Pentaerythrytyl Tetrastearate | 1.5 |
| FD&C Yellow (as 1.0% sol'n.) | 0.03 |
| Fragrance | 0.5 |
| Methyl paraben | 0.2 |
| Propyl paraben | 0.1 |
| Tocopherol Acetate | 0.05 |

Note: The above conditioning formulation was applied to 2.0 g tresses of pre-cleaned virgin brown human hair in the amount of 2.5 g per tress. The maximum tress diameter, as determined by measuring the work required to pull a tress through a series of templates of decreasing diameter and extrapolating to zero work, was found to increase by approximately 17% for hair treated with the above conditioning formulation. In a control study, a second set of identical tresses was treated with a commercially available conditioner marketed at retail under the trademark Finesse®. The maximum diameter of the tresses treated with the commercial conditioner was found to decrease by approximately 15%. This type of decrease is typical for known conditioning agents and is also a well-known phenomenon for commercially available conditioners containing polydimethylsiloxanes. The effect of increasing hair tress diameter of the conditioning formulation tested above is transferable to other cosmetic formulations such as conditioning shampoos, styling gels, mousses and the like.

Cosmetic Formulations; Hair Conditioning Formulation Evaluations: The hair conditioning formulation of cosmetic formulation A was duplicated with an ester functionalized MQ resin, Resin D (prepared according to U.S. Pat. No. 5,334,737, hereby incorporated by reference), replacing Resin A, and water replacing Resin A and compared to a commercially available conditioning composition, Finesse®, available at retail.

The conditioning formulation was applied to 6 inch, 2.0 g tresses of pre-cleaned virgin brown human hair in the amount of 2.5 g per tress. The conditioning formulation was allowed to remain on the hair for approximately one minute, then rinsed for thirty seconds under flowing tap water at a temperature of approximately 30°–35° C. The wet tresses were combed through ten times per side, and then dipped into a beaker of water three times, the excess water being squeezed out between the fingers. This process was performed in order to introduce a random degree of tangling to the tresses. The results of the combing measurements are presented in the following table:

TABLE 3

Combing Evaluations of Conditioned Human Hair

| Product | Initial Work (joules) | Final Work (joules) |
|---|---|---|
| Finesse ® | 0.134 | 0.0201 |
| Formulation A using Resin D | 0.147 | 0.0202 |
| Formulation A using Resin A | 0.132 | 0.0270 |

Notes: Combing evaluations were performed by means of a Diastron instrument model MTT600, using a crosshead speed of 30 mm/min., and a 2000 g load cell according to a modified method of Garcia and Diaz, J. Soc. Cosmet. Chem. vol. 27, pages 379–98 (1976).

The volumizing benefit of the conditioning formulation was analyzed using 6 inch 2.0 g tresses according to a modified procedure of Robbins and Crawford, J. Soc. Cosmet. Chem. vol. 35, pages 36–9 (1984). The work required to pull a tress through a series of templates of decreasing diameters was measured by means of a Diastron instrument model MTT600 at a speed of 50 ram/min. The maximum tress diameter was determined by extrapolating to zero work. The results are presented in the following table.

TABLE 4

Volume Changes in Hair Treated with Various Conditioning Formulations

| Product Difference | Initial Diameter | Final Diameter | % |
|---|---|---|---|
| Formulation A using water | 29.0 mm | 28.2 mm | −2.8 |
| Finesse ® | 36.9 mm | 31.2 mm | −15.4 |
| Formulation A using Resin D | 31.2 mm | 29.2 mm | −6.4 |
| Formulation A using Resin A | 31.2 mm | 36.4 mm | +16.7 |

The commercially available product produced a decrease in maximum tress diameter of approximately 15%. This decrease typically occurs with known conditioning agents. The conditioner base itself provides only a slight reduction in tress volume. The Resin D formulation performs like a general use conditioner, i.e. reducing combing forces and tress volume. The conditioning formulation containing the alkyl MQ, resin A, produced a surprising and unexpected result based on previous experience, i.e. a conditioning benefit and an increase in hair tress volume.

Conditioning Shampoo Formulations: A 2-in-1 shampoo formulation was prepared using Resin A and replacing Resin A with an emulsion of trimethylsilylamodimethicone, a known conditioning agent. The formulation employing trimethylsilylamodimethicone was prepared to serve as a control

TABLE 5

Conditioning Shampoo (2-in-1) Formulation Composition, Cosmetic Composition A2.

| Material Wt. % | Resin A Shampoo | Control Shampoo |
|---|---|---|
| Deionized water | 40.82 | 39.82 |
| Ammonium Lauryl Sulfate (25% sol'n) | 24.00 | 24.00 |
| Ammonium Laureth Sulfate (28% sol'n) | 14.30 | 14.30 |
| Cocamidopropyl Betaine (35% sol'n) | 11.43 | 11.43 |
| Lauramide DEA | 2.00 | 2.00 |
| Cocamide DEA | 2.50 | 2.50 |
| Resin A | 3.00 | 0.00 |
| Emulsion of Trimethylsilylamodimethicone | 0.00 | 4.00 |
| Dimethicone Copolyol | 1.00 | 1.00 |
| Guar Hydroxypropyltimonium Chloride | 0.75 | 0.75 |
| Methyl paraben | 0.15 | 0.15 |
| Propyl paraben | 0.05 | 0.05 |

Two 6 inch, 2.0 g tresses of virgin brown human hair were washed with the above conditioning shampoos and evaluated (duplicate samples) for combing force and hair tress volume.

TABLE 6

Evaluation of Conditioning Shampoo Formulations

| Measurement Control | Resin A Shampoo | 2-in-1 Shampoo |
|---|---|---|
| Combing Force (joules) | | |
| Initial | 0.214 | 0.220 |
| Final | 0.189 | 0.152 |
| Percent Decrease | 12 | 31 |
| Volume Measurement (mm) | | |
| Initial | 30.9(31.4) | 36.9 |
| Final | 31.8(31.4) | 34.0 |
| Percent Change | +3.0(0.0) | −8.0 |

Initial evaluations of two samples gave conflicting results, therefore additional measurements were performed on two additional samples of hair tresses to substantiate volume increases. The results presented inside the parentheses in Table 6 are averages of all four of the experimental results obtained on hair tress volume measurements using the resin of the invention. The results presented in front of the parentheses are averages of the three tress measurements showing an increase in hair volume. The results indicate an advantage for using the siloxysilicate MQ resin, Resin A, in place of the trimethylsilylamodimethicone emulsion. The shampoo formulation utilizing resin A is more properly characterized as a 3-in-1 shampoo providing cleaning, conditioning, and volumizing benefits. This is an unexpected result since, conditioning shampoos typically reduce hair tress volume when imparting a conditioning effect to the hair.

Cosmetic Formulation B: Cuticle Coat: Cuticle coats are formulations designed to impart or enhance shine on hair. Additionally, cuticle coats frequently reduce both triboelectric charging effects, i.e. fly-away hair, and combing forces, by adding a lubricious coating to the hair shaft, thus lowering both interfiber friction and electrostatic repulsion between the fibers. One method of imparting or increasing apparent luster or gloss on the hair is to coat the hair with a material having a high refractive index. Using this technique the apparent gloss or shine will be proportional to the refractive index of the material on the fiber surface. Absent other factors, a direct proportionality exists between refractive index and apparent shine on hair. Thus higher refractive index cuticle coating formulations will tend to impart a higher shine on hair. A cuticle coating preparation was prepared as follows:

TABLE 7

Cosmetic Formulation B

| Component | Amount (Wt. %) |
|---|---|
| Cyclomethicone (and) Dimethicone | 60.0 |
| Resin B | 30.0 |
| Isohexadecane | 10.0 |

Subjective evaluations indicate the formulation increased the apparent luster of human hair to which this formulation was applied by approximately 55% over the control.

Curl Retention with Polyether Modified MQ Resin, Polyetherdimethylsiloxysilicate: Polyetherdimethylsiloxysilicate is a clear, amber water soluble liquid. This material was evaluated for curl retention against a tap water control. Two 2 g 6 in. tresses were shampooed with a commercially available non-conditioning shampoo for 60 sec and rinsed under running, warm tap water for 30 sec. The control tress was wrapped around a glass rod having a diameter of 2.4 cm, securing the ends of the tress with elastic bands. The second tress was treated with an excess of the aqueous 10% solution of the Polyetherdimethylsiloxysilicate after shampooing. The excess liquid was squeezed out between the fingers and the tress was curled around a glass rod having a diameter of 2.4 cm. Both tresses were allowed to air dry overnight.

The tresses were removed from the glass rods, suspended from an acrylic board and the length of each tress was measured over a period of 24 hours. Percent curl retention values were evaluated according to the following relationship:

$$\text{Percent Retention}=100-(L_f-L_i)/L_i$$

where $L_i$ is the hair tress length at t=0 and $L_f$ is the length at time t.

TABLE 8

Curl Retention Evaluation for Hair Treated with 10% Aqueous polyetherdimethylsiloxysilicate (MQ)

| Time (hrs.) | Water Control | MQ Treated |
|---|---|---|
| 0.5 | 91.5 | 100.0 |
| 1.0 | 85.9 | 100.0 |
| 2.0 | 77.5 | 97.8 |
| 3.0 | 70.4 | 97.8 |
| 4.0 | 70.4 | 97.8 |
| 5.0 | 63.4 | 93.4 |
| 6.0 | 59.2 | 93.4 |
| 24.0 | 49.3 | 89.0 |

These measurements were taken under ambient conditions of 76° F. and 24% relative humidity.

It is expected that incorporation of polyetherdimethylsiloxysilicates of the present invention into various hair treating cosmetic formulations would thus impart curl retention benefits to the formulation. Thus for example a 2-in-1 shampoo incorporating polyetherdimethylsiloxysilicate would be a 3-in-1 shampoo having cleaning, conditioning and curl retention properties. Addition of polyetherdimethylsiloxysilicate to a 3-in-1 shampoo having cleaning, conditioning, and volumizing properties would result in the preparation of a 4-in-1 shampoo having cleaning, conditioning, volumizing, and cud retention properties. Hair conditioners, mousses, fixatives, spritzes and the like incorporating polyetherdimethylsiloxysilicate would be expected to show improved curl retention properties.

Having described the invention that which is claimed is:

1. A resin of the formula:

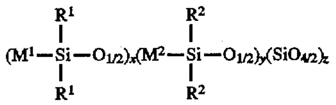

where both $R^1$ and $R^2$ are either a phenyl group or an alkyl group having from 1 to 12 carbon atoms, and both $M^1$ and $M^2$ are independently selected from the group consisting of phenyl, phenethyl, and polyether subject to the limitation that the ratio of the subscripts x, y, and z satisfies (x+y)/z equal to about 2 where z ranges from 1 to about 30 and x and y may be zero or a positive number subject to the limitation that when $M^1$ is a polyether $M^2$ is also a polyether.

2. The resin of claim 1 wherein the viscosity of the resin ranges from about 50 to approximately 1,000 centistokes at 25° C.

3. The resin of claim 1 where $R^1$ is alkyl and $R^2$ is phenyl.

4. The resin of claim 1 wherein $M^1$ and $M^2$ are the same and $M^1$ is produced by hydrosilylation from a starting material selected from polyethers having the formula:

$$H_2C{=}C{-}CH_2R^3{-}(O{-}CHR^4{-}CH_2)_u{-}(OCH_2CH_2)_v{-}OR^5$$

where $R^3$ is $-(CH_2)_n-$ where n ranges from 1 to about 20, $R^4$ is a one to twenty carbon alkyl group, and $R^5$ is selected from the group consisting of H, $-CH_3$, and $-C(O)CH_3$; and where u and v are integers ranging from 0 to 20 subject to the limitation that u+v≧1.

5. The resin of claim 4 wherein the viscosity of the resin ranges from about 50 to about 1,000 centistokes at 25° C.

6. The resin of claim 4, wherein $R^1$ is methyl and $R^2$ is methyl.

7. An emulsifier for oil-in-water emulsions comprising the resin of claim 4.

* * * * *